(12) United States Patent
Elders et al.

(10) Patent No.: US 7,987,711 B2
(45) Date of Patent: Aug. 2, 2011

(54) DEVICE AND METHOD FOR DIAGNOSING A DISORDER

(75) Inventors: Leonardus Antonius Maria Elders, Rotterdam (NL); Johannes Gerardus Steenkamer, Rotterdam (NL)

(73) Assignee: Consulo B.V., Rotterdam (NL)

( * ) Notice: Subject to any disclaimer, the term of this patent is extended or adjusted under 35 U.S.C. 154(b) by 150 days.

(21) Appl. No.: 12/528,270

(22) PCT Filed: Feb. 19, 2008

(86) PCT No.: PCT/NL2008/050093
§ 371 (c)(1),
(2), (4) Date: Aug. 21, 2009

(87) PCT Pub. No.: WO2008/103037
PCT Pub. Date: Aug. 28, 2008

(65) Prior Publication Data
US 2010/0095764 A1     Apr. 22, 2010

(30) Foreign Application Priority Data
Feb. 22, 2007  (NL) .................................... 2000501

(51) Int. Cl.
*A61B 1/24* (2006.01)
(52) U.S. Cl. .................................. 73/379.02

(58) Field of Classification Search ............... 73/379.02, 73/379.01, 152.48; 128/687; 600/587; 356/71
See application file for complete search history.

(56) References Cited

U.S. PATENT DOCUMENTS

| | | |
|---|---|---|
| 3,346,108 A | 10/1967 | Wizelman |
| 3,540,067 A | 11/1970 | Deruaz |
| 3,923,222 A | 12/1975 | Groves |
| 4,347,852 A * | 9/1982 | Tan ............................. 600/500 |
| 4,718,874 A | 1/1988 | Warren |
| 5,056,530 A * | 10/1991 | Butler et al. .................. 600/587 |
| 5,926,261 A * | 7/1999 | Hoshino ......................... 356/71 |
| 6,905,064 B1 | 6/2005 | Ong |
| 2002/0189049 A1 | 12/2002 | Freidell |

FOREIGN PATENT DOCUMENTS

| | | |
|---|---|---|
| GB | 1321665 A | 6/1973 |
| JP | 2006282273 A | 10/2006 |
| WO | 0076347 A | 12/2000 |

* cited by examiner

*Primary Examiner* — Jewel Thompson
(74) *Attorney, Agent, or Firm* — Fliesler Meyer LLP

(57) ABSTRACT

A device (1) for diagnosing a disorder comprises a stop for stopping a human extremity (5), such as a finger, when said extremity exerts a force on the stop. Detection means are provided for detecting said exerted force. The device has a support member (20) for supporting the stop. The stop comprises one or more resilient strips (8,17), each of which projects from the support member up to in each case a free end. The resilient strips are arranged substantially parallel to and at a distance from one another. Each resilient strip can, by being deformed, contact an adjacent resilient strip.

16 Claims, 3 Drawing Sheets

DEVICE AND METHOD FOR DIAGNOSING A DISORDER

Figure 1A:
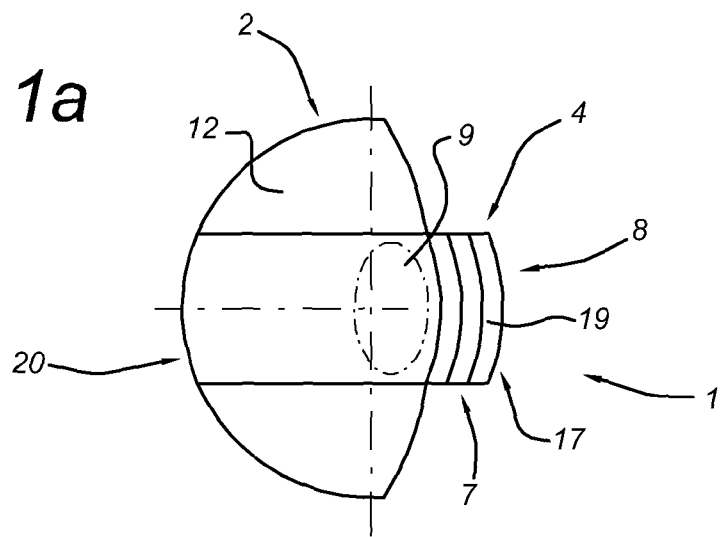

The invention relates to a device for diagnosing a disorder, such as a CANS disorder. The expression CANS disorder is understood to mean complaints or symptoms on arms, neck and shoulders. These disorders comprise, for example, inflammations of the tendon, inflammations of the bursa, inflammations of the bones and joints, and disorders of the peripheral sinews. Diagnosing a disorder is making a diagnosis by a person who may or may not be medically qualified. A diagnosis may, for example, be made by a doctor or nurse, but also by a patient or employee himself or herself.

Diagnosing disorders on the arms, neck and shoulders is difficult. Not every disorder has a unique pattern of symptoms, that is to say the symptoms of different disorders may overlap. In addition, if pain symptoms have been diagnosed, the correct treatment can only be prescribed if the disorder has been located. Locating the disorder may form part of diagnosing it. It is particularly difficult with a CANS disorder to accurately determine the location of the pain symptoms in the area of the arms, neck or shoulders. Diagnosis of the disorder is continued during the treatment in order to monitor an increase or decrease in the pain symptoms.

It is an object of the invention to provide an improved device for diagnosing a disorder, in particular a CANS disorder.

This object is achieved according to the invention by a device for diagnosing a disorder comprising a base, which is provided with a lower side, which defines a support surface for resting on a flat surface, such as a tabletop, and a stop member, which is arranged on the base, which stop member is provided with a bottom surface which faces towards the lower side of the base and is designed to stop a human finger when said finger exerts a force on said bottom surface, and in which the bottom surface extends substantially parallel to and at a distance from the support surface defined by the lower side of the base, and the distance between the bottom surface and the support surface is substantially smaller than 2 cm.

The lower side of the base defines a support surface for resting on a flat surface, such as a tabletop. This will be referred to by the term "flat lower side". Obviously, the lower side of the base may be smooth or provided with a cavity, ridges, recesses or relief in order to increase the friction between the lower side of the base and the tabletop.

During a diagnosis treatment using the device according to the invention, the lower side of the base rests on a flat surface, such as a tabletop. A person inserts a finger between the tabletop and the pressure face or bottom surface of the stop member. Due to the distance of 2 cm between the tabletop and the pressure face, the finger is in the zero position, while the finger virtually immediately bears against the pressure face if it is moved upwards. The distance of 2 cm is particularly suitable for measuring a force exerted by a finger.

In order to diagnose a disorder, said person applies a pressure force on the bottom surface with said finger. This forms a counterpressure test for the tendons, in particular flexors and extensors of said finger, which run to the wrist, forearm and elbow. The pressure force exerted by said person can be detected. As a result thereof, it is possible to measure—in a qualitative and/or quantitative manner—how great a maximum force the user is able to exert. While the test is being carried out, the person can, at the same time, indicate whether any pain occurs, where the pain occurs and the intensity thereof, so that any possible disorder can be detected.

It should be noted that an apparatus for testing the strength of muscles or muscle groups is known from WO 87/07129. This apparatus has a support frame with a vertical guide post, to which a support arm is connected in a height-adjustable manner. A force sensing device is connected to the support arm. The force sensing device can measure the force which a person exerts with, for example, a fist, knee or thigh. However, this apparatus is unsuitable for testing finer, individual muscles, such as the muscles in the fingers. Diagnosing a CANS disorder by measuring a force exerted by a finger is not possible. In particular, it is not possible to locate pain symptoms in the area of the arms, neck and shoulders with this apparatus.

By contrast, the device according to the invention has a support surface on the lower side of the base and a pressure face or bottom surface for applying a force thereon by a finger and the distance between the support surface and the pressure face is smaller than 2 cm. If the support surface and a finger of a person are on the same flat surface, such as a tabletop, said finger can readily be placed below the bottom surface. At the same time, the distance of at most 2 cm is so small that said finger will press against the bottom surface virtually immediately when it is moved upwards. Diagnosing starts from the zero position of the finger, that is to say the rest position. If the distance between the tabletop and the pressure face were greater, the finger would already be slightly prestressed in an upward direction. This would result in a refined measurement and associated diagnosis being less accurate.

A disorder is usually accompanied by a loss of force in the finger. The device according to the invention may be provided with detection means for detecting the force exerted. Said detection means are suitable for detecting the force exerted by a finger at a first point in time and the force exerted by said finger at a second point in time. The forces exerted at those two points in time can be compared to one another.

As a result thereof, it is possible to prevent disorders and/or symptoms by means of the device according to the invention. If the maximum force exerted by the person examined decreases over time, this is an indication that he or she is developing one of the abovementioned disorders. Consequently, said person can take measures to prevent the disorder from developing further. Therefore, said device according to the invention can also be used as a means for preventing a disorder from developing.

In addition, the device according to the invention is suitable for monitoring a disorder during its treatment. To this end, the progress of a disorder which has already developed can be followed and made visible.

Incidentally, the device according to the invention is not limited to use by medically trained staff. The device can be used by any person, including the patient himself or herself. The device according to the invention then is a self-care aid.

In one embodiment of the invention, the stop member comprises at least one projecting part which projects laterally with respect to the base. The projecting part forms an overhanging part of the stop member. The pressure face or bottom surface of the stop member is situated under the projecting part.

In one embodiment of the invention, the stop member is provided with a support member which is arranged on the base, and at least one resilient strip, which projects transversely from the support member up to a free end. The resilient strip is suspended from the support member in such a manner that the strip projects transversely with respect to the support member. The strip forms a leaf spring element. The deflection of the strip at its free end is a measure of the pressure force exerted on the strip, that is to say the strip not only comprises the pressure face of the stop member, but also forms detection means for detecting the force exerted.

However, according to the invention, the detection means may be designed in various ways. For example, the detection means comprise an electronic pressure sensor, which can measure the force exerted by the finger.

According to the invention, it is possible that the stop member comprises several resilient strips, each of which projects from the support member up to in each case a free end, with the resilient strips being arranged substantially parallel to and at a distance from one another, and with each resilient strip being able to contact an adjacent resilient strip by preferably elastically deforming the former. The distance between the resilient strips is, for example, between 0.5-2 mm, such as approximately 1 mm. The number of resilient strips which have been pushed against one another is a measure of the force exerted. In this embodiment, the detection means are therefore made up of several strips. The strips can objectively measure the force exerted by a finger. The measurement is in addition reproducible.

Each of the resilient strips may have a length which is defined by the distance between the support member and the free end, with the length of the resilient strips with respect to one another being different. For example, the bottommost strip extends furthest from the support member, while the strips arranged above it are in each case slightly shorter.

The length of each resilient strip is, for example, between 20-60 mm. The force required to deform a strip increases as the length of said strip decreases.

In one embodiment of the invention, the base is provided with at least one securing part which projects at least partially, for example laterally, with respect to the stop member, in particular the support member and/or the resilient strips. The base can be secured to a flat surface, such as a tabletop, by pressing the projecting securing part against said surface.

If the base is provided with two securing parts which project laterally, on opposite sides of the base with respect to the stop member, the device can be secured in a very sturdy manner on the tabletop or another flat surface.

According to the invention, the device may be produced in one piece. The device is, for example, integrally formed from plastic, such as polystyrene. Consequently, the weight of the diagnosing device is extremely low—the device according to the invention is readily portable.

The invention also relates to an assembly comprising an object having a flat surface, such as a tabletop, and a device as described above, in which the lower side of the base is arranged on the flat surface. The flat surface extends, for example, substantially horizontally and is particularly suitable for completely supporting the forearm of a person which is arranged thereon.

The invention furthermore relates to a method for diagnosing a disorder, comprising providing an assembly as described above, exerting a force by a finger on the bottom surface of the stop member of the device, detecting whether pain or loss of force occurs when exerting said force. The force exerted on the pressure face or bottom surface preferably is a pressure force which is directed substantially away from the tabletop. In case pain is felt or loss of force detected, the user may be asked, with regard to his or her history, where said pain is felt in the body, for example the elbow, forearm, wrist or fingers.

Further characteristics of the method according to the invention are described in the dependent claims 12-16. In addition, the method may comprise placing a human extremity on the surface in such a manner that the extremity is situated on a top surface opposite the bottom surface or farther pressure face of the stop member, for example a resilient strip thereof, and exerting a pressure force on said top surface using said extremity. The method may also comprise placing a hand on the surface, placing one side of the hand on said top surface in such a manner that the little finger is turned towards the surface, exerting a pressure force on said top surface using said side of the hand.

The invention will now be described in more detail, and only by way of example, with reference to the drawing.

FIGS. 1*a*, *b* and *c* show a diagrammatic top, side and front view, respectively, of a device for diagnosing a disorder according to the invention.

Figure 2:
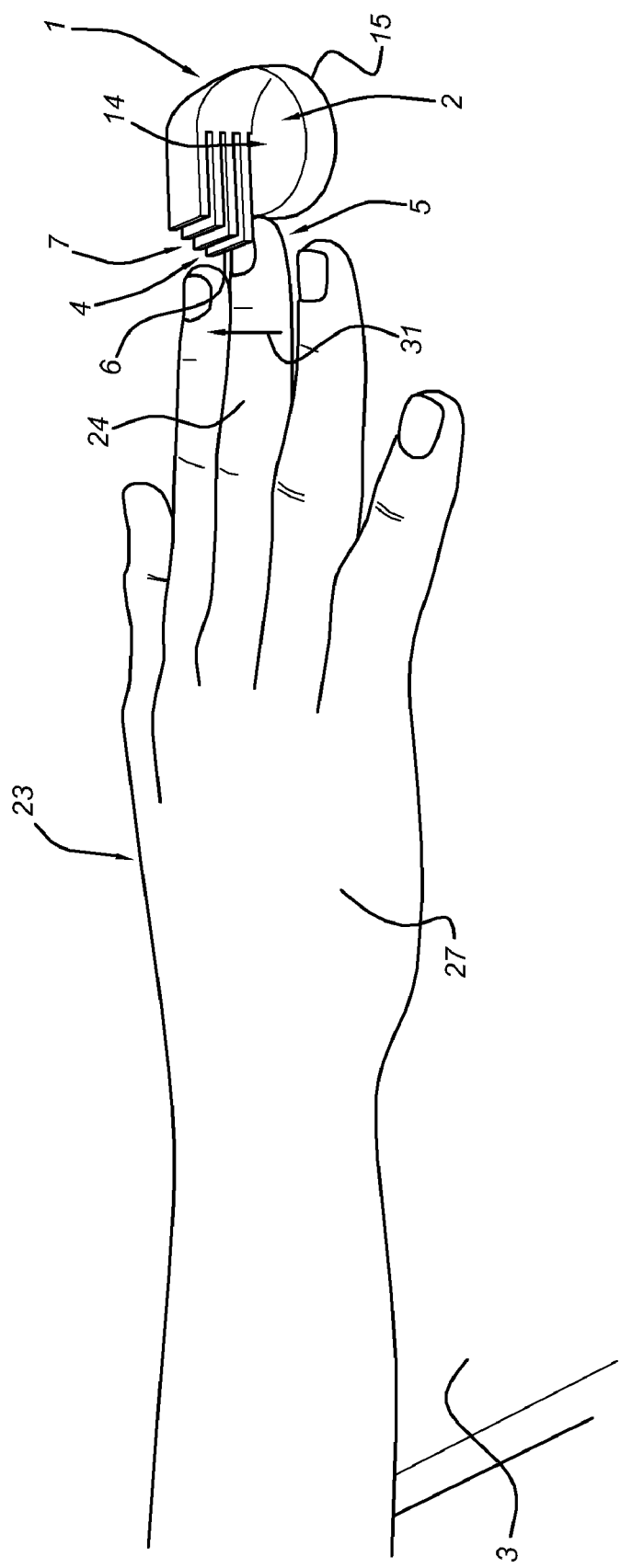

FIG. 2 diagrammatically shows a first embodiment of a method for diagnosing a disorder according to the invention using the device illustrated in FIGS. 1*a*, *b* and *c*.

Figure 3:
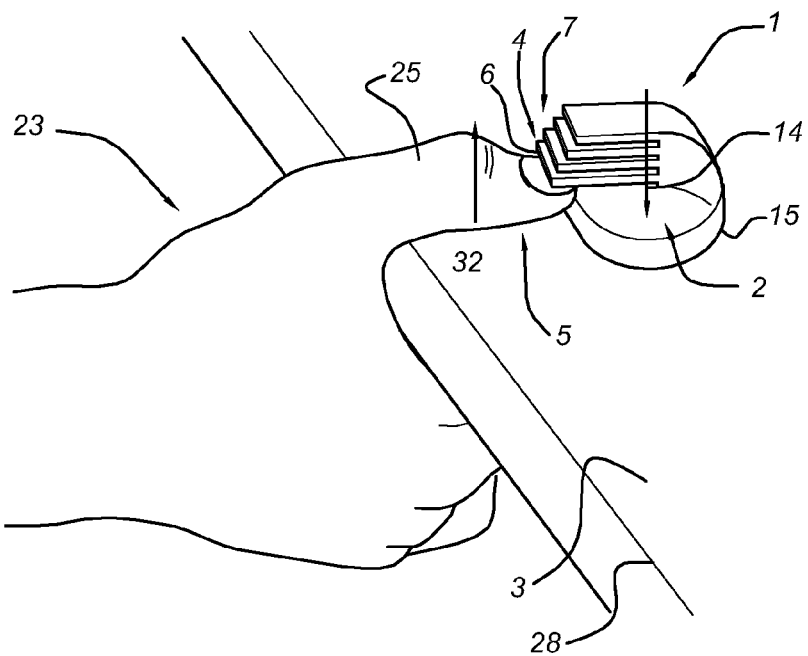

FIG. 3 diagrammatically shows a second embodiment of a method for diagnosing a disorder according to the invention using the device illustrated in FIGS. 1*a*, *b* and *c*.

Figure 4:
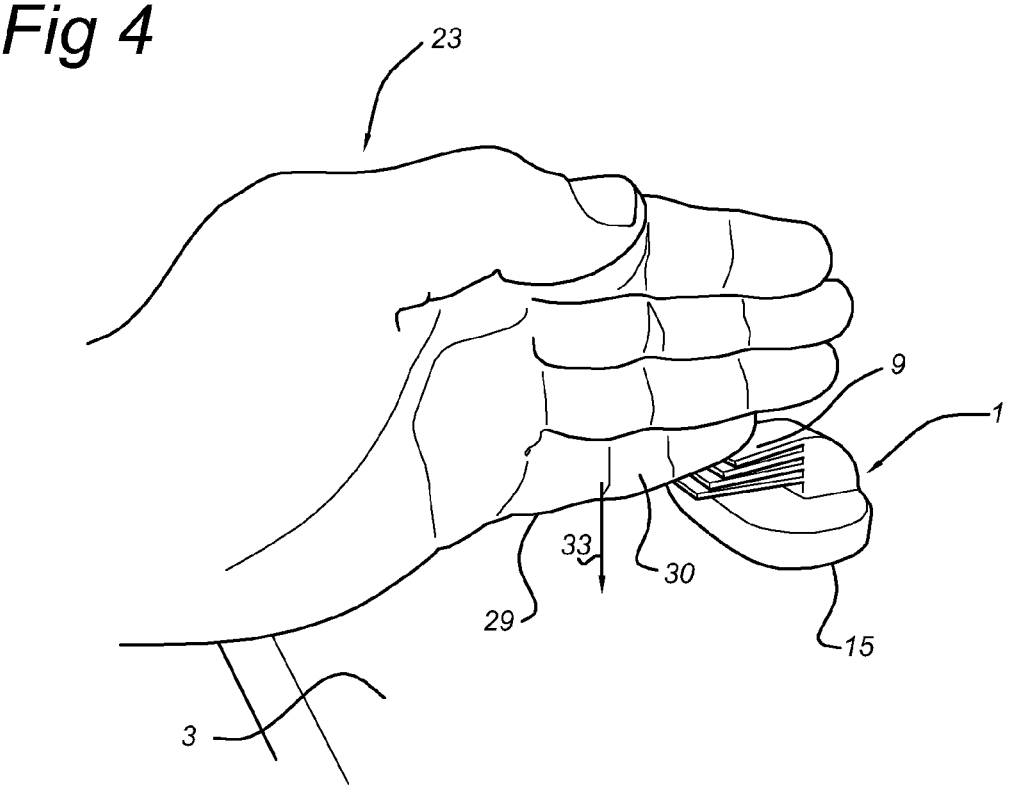

FIG. 4 diagrammatically shows a third embodiment of a method for diagnosing a disorder according to the invention using the device illustrated in FIGS. 1*a*, *b* and *c*.

Figure 1B:
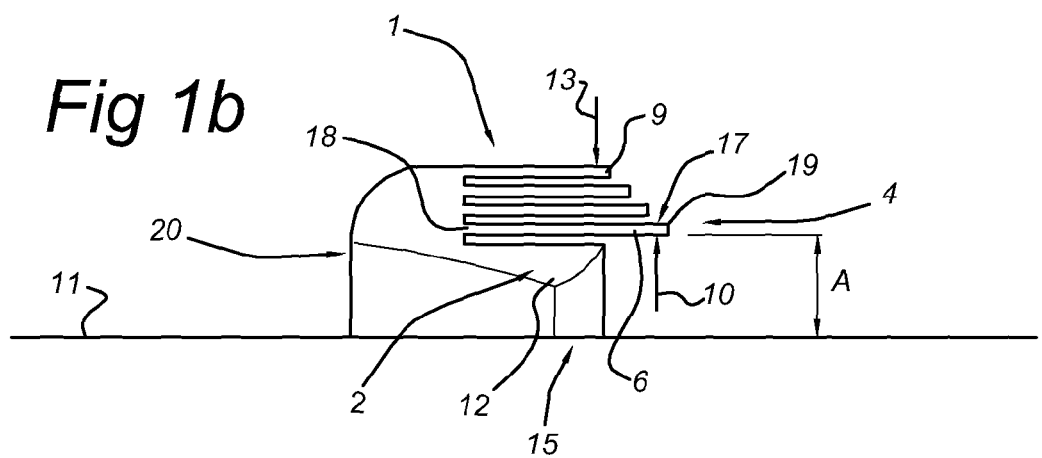
Figure 1C:
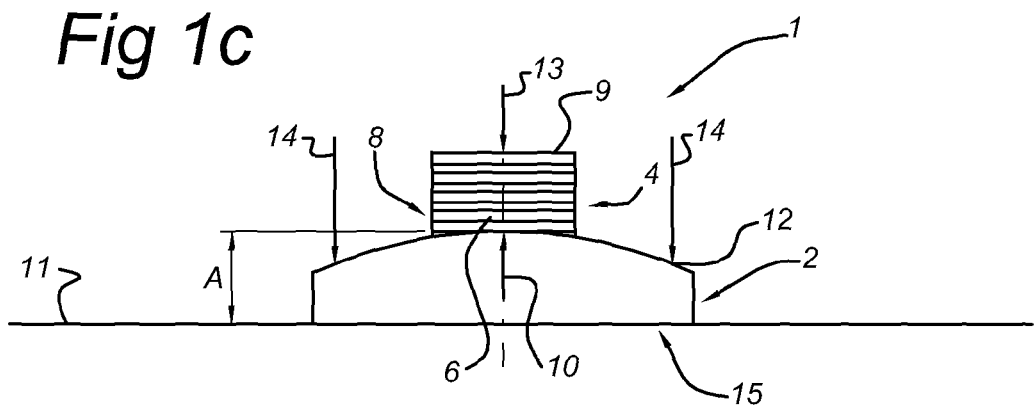

The device for diagnosing a disorder according to the invention is denoted overall in FIG. 1 with reference numeral 1. The device 1 according to the invention is extremely compact. As a result, a person can readily handle the device 1 and carry it with him or her.

The device 1 comprises a base or foot 2. The base 2 has a flat lower side 15. The flat lower side 15 forms a support surface for stably resting on a flat surface 3, such as a tabletop. The base 2 has laterally projecting parts 12, which can be pressed against the surface 3 (see arrow 14). As a result, the device 1 can be secured before use. The device 1 may be secured permanently or detachably, for example by hand.

The device 1 comprises a stop member which, in this exemplary embodiment, is provided with a stop 4 and a support member 20 for supporting the stop 4. The support member 20 is arranged on the base 2. The stop 4 comprises a pressure face or bottom surface 6 for exerting a pressure force thereon by means of a human extremity, such as a finger 5. The pressure face 6 faces towards the base 2 and runs parallel to and at a distance from the flat lower side 15. The pressure face 6 is at a distance A from the flat lower side 15. The direction of the force to be exerted on the pressure face 6 is indicated by arrow 10.

In this exemplary embodiment, the stop 4 comprises several resilient strips 8,17. The flat lower side 15 runs substantially parallel to and at a distance from the resilient strips 8,17. The resilient strips 8,17 form a series of leaf springs, which are arranged at a distance from one another and parallel one above the other. The resilient strips 8,17 each have a fixed end 18. The fixed ends 18 of the strips 8,17 are attached to the support member 20, which is arranged on the base 15. The strips 8,17 project transversely from the support member 20. Each strip 8,17 has a free end 19 opposite the fixed end 18. The pressure face 6 is situated near the free end 19 of the bottommost strip 8.

When a pressure force 10 is being exerted on the pressure face 6, a part of the strips 17 is pushed together due to being deformed. The number of strips 17 which are pushed together forms an indication for the pressure force exerted on the pressure face 6. The strips 17 are therefore detection means for detecting said force.

The distance between the pressure face, which is formed by the bottom surface of the bottommost strip 8, and the flat lower side 15 of the base 2 is sufficiently large to accommodate a human extremity, such as a finger or thumb, lying under said strip. In addition, said distance is smaller than 20 mm. As a result thereof, the clearance between the human extremity and the pressure face 6 is limited.

The device 1 comprises a further pressure face 9. The further pressure face 9 is turned away from the lower side 15 of the base 2, i.e. is directed upwards in FIGS. 1a-c. The direction of a pressure force exerted on the further pressure face 9 is indicated by arrow 13. As a result thereof, one or more strips 17 come to lie against each other. The number of strips 17 which have been pushed together is a measure of the force exerted. The second pressure face 9 is suitable for diagnosing specific disorders.

FIG. 2 shows an embodiment of the method according to the invention, in which use is made of a device 1 from FIG. 1 which is positioned on a surface 3 and in a use position. This method for diagnosing a disorder comprises providing a device 1 which is arranged on a surface 3 in such a manner that the lower side 15 is on the surface 3 and the pressure face 6 is at a distance (A in FIG. 1) from the surface 3 and is turned towards the surface 3. Then, a human extremity 5 is placed on the surface 3 in such a manner that it is situated between the surface 3 and pressure face 6, following which the person places his or her extremity 5 against the pressure face 6 and moves it in the direction of arrow 31. In this case, said extremity 5 exerts a pressure force on the pressure face 6 (10 in FIG. 1).

In FIG. 2, the extremity 5 is a finger 24 of a hand 23. The hand 23 is in this case placed on the surface 3 with the fingers 24 extended. The palm of the hand 23 here rests against the surface 3, with the forearm also lying on the surface 3. It is also possible for the hand 23 to be placed on the surface 3 in such a manner that the back 27 of the hand 23 is situated on the surface 3 (not illustrated).

FIG. 3 shows an embodiment of the method according to the invention, in which use is made of a device 1 from FIG. 1 placed on a surface 3 and in a use position. This method for diagnosing a disorder comprises placing a device 1 along an edge 28 of the surface 3. The lower side 15 in this case rests on the surface 3, while the pressure face 6 is located at a distance (A in FIG. 1) from the surface 3 and is turned towards the surface 3. Then, a thumb 25 is positioned in such a manner that the thumb 25 extends from the edge 28 and is situated between the surface 3 and pressure face 6, following which said thumb 25 is placed against the pressure face 6. The thumb 25 is moved further in the direction of arrow 32—in this case, said thumb 25 exerts a pressure force (10 in FIG. 1) on the pressure face 6.

FIG. 4 shows an embodiment of the method according to the invention, in which use is made of a device 1 from FIG. 1 placed on a surface 3 and in a use position. The method for diagnosing a disorder comprises providing a device 1 which is situated on a surface 3 in such a manner that the support surface 15 is on the surface 3 and the further pressure face 9 is turned away from the surface 3. A human extremity 5 is placed on the surface 3 in such a manner that the extremity 5 is situated on the further pressure face 9. The person then pushes said extremity 5 onto the further pressure face 9.

In FIG. 4, the hand 23 is placed on the surface 3 in such a manner that the side 29 of the hand 23 bears against the further pressure face 9. The little finger 30 is situated nearest the surface 3. Subsequently, a pressure force (13 in FIG. 1) is exerted on said further pressure face 9 using said side 29 of the hand 23. In this case, the side 29 of the hand 23 is moved in the direction of arrow 33. As is illustrated, when said pressure force is exerted on the further pressure face 9, various strips are moved against one another. The number of strips contacting one another is an indication of the magnitude of the pressure force exerted on the further pressure face 9. This analogously also applies to the pressure force exerted on the pressure face 6. The method of FIGS. 2-4 may comprise the qualitative (non-absolute) or quantitative measurement of the magnitude of the pressure force exerted on the pressure face 6 or further pressure face 9 (10 or 13).

The device and method according to the invention may be used for diagnosing, for example, the following disorders: epicondylitis lateralis, epicondylitis medialis, loss of force in fingers, mallet finger, DeQuervain syndrome, osteoarthritis of the wrist joint, flexor carpi ulnaris tendinitis, post-traumatic dystrophy, arthrosis, degenerative disorders, dystonia, rheumatoid arthritis, gout, fibromyalgia, trigger finger, intersection syndrome, myofascial pain syndrome, flexor carpi radialis tendinitis, flexor (pre)tendinitis/(teno)synovitis, extensor (pre)tendinitis/(teno)synovitis, Dupuytren's contracture, olecranon bursitis, radial tunnel syndrome, double crush syndrome, Linburg syndrome and Guyon's canal syndrome.

The invention furthermore relates to a device, assembly and method comprising any possible combination of the features described in this description and/or illustrated in the drawings.

The invention also relates to a device for diagnosing a disorder, comprising:
 a stop for stopping a human extremity, such as a finger, when said extremity exerts a force on the stop, and
 detection means for detecting said exerted force,
in which a support member is provided for supporting the stop, and the stop comprises at least one resilient strip, which projects transversely from the support member up to a free end, in which the support member is arranged on a base, which is provided with a flat lower side which runs substantially parallel to and at a distance from the resilient strip or strips, in which the strip turned towards the base is provided with a pressure face or bottom surface, which is arranged parallel to and at a distance from the flat lower side, and in which said distance between said bottom surface and the lower side is smaller than 20 mm.

In this case, it is possible that the base is provided with at least one securing part which at least partially projects with respect to the support member and/or the resilient strip or strips.

It will be clear to those skilled in the art that many variants of the device, assembly and method according to the invention are possible which are within the scope of the invention.

The invention claimed is:

1. A device (1) for diagnosing a disorder comprising:
 a base (2), which is provided with a lower side (15), which defines a support surface for resting on a flat surface, such as a tabletop, and
 a stop member (4,20), which is arranged on the base (2), which stop member (4,20) is provided with a bottom surface (6) which faces towards the lower side (15) of the base (2) and is designed to stop a human finger (5) when said finger (5) exerts a force on said bottom surface (6), and in which the bottom surface (6) extends substantially parallel to and at a distance from the support surface defined by the lower side (15) of the base (2), and the distance between the bottom surface (6) and the support surface is substantially smaller than 2 cm.

2. The device as claimed in claim 1, in which the stop element (4,20) comprises at least one projecting part (8,17) which projects laterally with respect to the base (2).

3. The device as claimed in claim 1 or 2, in which the stop member (4,20) is provided with a support member (20) which is arranged on the base (2), and at least one resilient strip (8,17), which projects transversely from the support member (20) up to a free end (19).

4. The device as claimed in claim 3, in which the stop member (4,20) comprises several resilient strips (8,17), each of which projects from the support member (20) up to in each case a free end (19), in which the resilient strips (8,17) are arranged substantially parallel to and at a distance from one another, in which each resilient strip (8,17) can, by being deformed, contact an adjacent resilient strip (8,17).

5. The device as claimed in claim 4, in which the distance between the resilient strips (8,17) is between 0.5-2 mm, such as approximately 1 mm.

6. The device as claimed in claim 4 in which the resilient strips (8,17) each have a length which is defined by the distance from the support member (20) up to the free end (19), and in which the length of the resilient strips (8,17) with respect to one another is different.

7. The device as claimed in claim 6, in which the length of each resilient strip (8,17) is between 2-6 cm.

8. The device as claimed in claim 1, in which the base (2) is provided with at least one securing part (12) which projects laterally with respect to the stop member (4,20).

9. The device as claimed in claim 8, in which the base (2) is provided with two securing parts (12) which project laterally on opposite sides of the base (2) with respect to the stop member (4,20).

10. An assembly comprising an object having a flat surface (3), such as a tabletop, and a device (1) as claimed in claim 1, in which the lower side (15) of the base (2) is arranged on the flat surface (3).

11. A method for diagnosing a disorder, comprising:
providing an assembly as claimed in claim 10,
exerting a force by means of a finger (5) on the bottom surface (6) of the stop member (4,20) of the device (1),
detecting whether pain or loss of force occurs when exerting said force.

12. The method as claimed in claim 11, further comprising:
placing a forearm with a hand (23) on the flat surface (3) in such a manner that the forearm and the hand (23) rest on the surface (3) with the fingers (24) extended and that at least one finger (24) is situated between the flat surface (3) and the bottom surface (6) of the stop member (4, 20),
placing the finger (24) situated between the flat surface (3) and the bottom surface (6) against said bottom surface (6), and
exerting a pressure force (10) with said finger (24) on the bottom surface (6).

13. The method as claimed in claim 12, further comprising:
placing the hand (23) on the flat surface (3) in such a manner that the palm of the hand (23) is situated on the flat surface (3).

14. The method as claimed in claim 12, further comprising:
placing the hand (23) on the flat surface (3) in such a manner that the back (27) of the hand (23) is situated on the surface.

15. The method as claimed in claim 11 or 12, comprising:
placing a thumb (25) on the flat surface (3) in such a manner that the thumb (25) is situated between the surface (3) and pressure face (6),
placing said thumb (25) against the bottom surface (6) of the stop member (4,20), and
exerting a pressure force (10) on said bottom surface (6) using said thumb (25).

16. The method as claimed in one of claim 11, further comprising:
detecting the force exerted on the bottom surface (6) of the stop member (4,20).

* * * * *